United States Patent [19]

Ghazarossian et al.

[11] Patent Number: 5,180,828
[45] Date of Patent: Jan. 19, 1993

[54] CHROMOPHORIC REAGENTS FOR INCORPORATION OF BIOTIN OR OTHER HAPTENS INTO MACROMOLECULES

[75] Inventors: Vartan Ghazarossian; Viola T. Kung, both of Menlo Park; Robert F. Zuk, Burlingame, all of Calif.

[73] Assignee: Molecular Devices Corporation, Menlo Park, Calif.

[21] Appl. No.: 865,641

[22] Filed: Apr. 9, 1992

Related U.S. Application Data

[63] Continuation of Ser. No. 477,545, Feb. 9, 1990, abandoned.

[51] Int. Cl.$^5$ ............... C07D 491/16; C07D 513/04; G01N 33/543
[52] U.S. Cl. .................... 546/37; 435/7.5; 436/501; 548/304.1
[58] Field of Search ............ 548/303; 546/37

[56] References Cited

U.S. PATENT DOCUMENTS

| | | | |
|---|---|---|---|
| Re. 31,712 | 10/1984 | Giese | 427/214 |
| 4,228,237 | 10/1980 | Hevey et al. | 435/188 |
| 4,298,685 | 11/1981 | Parikh et al. | 435/188 |
| 4,467,031 | 8/1984 | Gallati et al. | 435/810 |
| 4,486,530 | 12/1984 | David et al. | 436/519 |
| 4,535,057 | 8/1985 | Dressman et al. | 436/808 |
| 4,550,075 | 10/1985 | Bacquet et al. | 435/188 |
| 4,551,550 | 5/1986 | Hafeman et al. | 435/4 |
| 4,582,810 | 4/1986 | Rosenstein | 436/528 |
| 4,632,901 | 12/1986 | Valkirs et al. | 435/5 |
| 4,656,025 | 4/1987 | Deutsch | 424/9 |
| 4,656,252 | 4/1987 | Giese | 530/350 |
| 4,704,353 | 11/1987 | Humphries et al. | 435/26 |
| 4,727,019 | 2/1988 | Valkirs et al. | 435/6 |

FOREIGN PATENT DOCUMENTS 259186 3/1988 European Pat. Off. .

OTHER PUBLICATIONS

D. Scott et al., Mol. Immunol., vol. 21, No. 11 (1984), pp. 1055-1060.
J. Immunoassay 4: 209-327, Ishikawa et al., 1983.
Clinical Chemistry 34/8: 1585-1590, Vilja et al., 1988.
Analytical Biochemistry 171:1-32, Wilcheck and Bayer, 1988.
Analytical Biochemistry 42:237-247, Samejima et al., 1971.
Colorimetric Determination of Biotin and Analogs, McCormick and Roth in Biotin and Derivatives, pp. 383-385.
Analytical Biochemistry 64:284-288, Snyder and Sobobocinski, 1975.
Nucleic Acids Research 13:745-761, Forster et al., 1985.
Biotechnology 5:269-272, McInnes et al., 1987.

*Primary Examiner*—Mary E. Ceperley
*Attorney, Agent, or Firm*—Allegretti & Witcoff, Ltd.

[57] ABSTRACT

Compounds and methods for detecting the incorporation of a hapten into a protein or macromolecules are disclosed. The compounds comprise haptens bound directly or indirectly to a chromophoric group and a macromolecules-reactive group, whereby incorporation of the hapten into a protein or other macromolecules may be detected. The disclosure includes a compound of the formula:

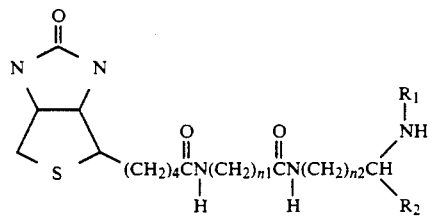

wherein
$n_1$ is 1, 2, 3, 4, 5, 6 or 7;
$n_2$ is 0, 1, 2, 3, 4, 5, 6 or 7;
$R_1$ is either a carboxytetramethyl-rhodamyl, sulforhodamyl 101, or dinitrophenylaminohexanoyl group; and
$R_2$ is —CO$_2$H, —NH$_2$, —SH,

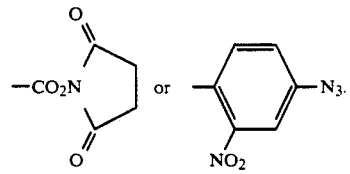

1 Claim, No Drawings

CHROMOPHORIC REAGENTS FOR INCORPORATION OF BIOTIN OR OTHER HAPTENS INTO MACROMOLECULES

This application is a continuation of application Ser. No. 07/477,545, filed Feb. 9, 1990 now abandoned.

BACKGROUND OF THE INVENTION

1. Field of the Invention

This invention relates to diagnostic reagents which are useful in detecting specifically binding complexes in solutions and assay methods using such reagents. The specifically binding complexes, sometimes referred to as ligand-receptor complexes, include DNA/single-strand-DNA-binding-protein complexes, antigen/antibody complexes (such as DNA/anti-DNA complexes), and similar specifically binding complexes. Methods of labeling compounds for the direct determination of haptens such as biotin, into macromolecules is the subject of this application.

2. The Related Art

There are extensive teachings in the art of diagnostic assays and reagents involving specifically binding complexes. Antigen/antibody reactions are widely used to determine antigen and antibodies. The labeling of members of these complexes with detectable markers such as enzymes or florescent dyes is well known. The binding of antigen or antibodies to solid supports as a means of removing complexes from solutions is also known. The use of haptens such as biotin and anti-haptens such as streptavidin in diagnostic assay is extensively discussed in a review article that appears in Anal. Biochem., 171:1-32 (Wilchek & Bayer, 1988).

The extensive use of avidin/biotin technology in immunology and diagnostic medicine is based on numerous factors. The high binding affinity between avidin and biotin yields an avidin-biotin complex having very high stability. Avidin is a tetrameric glycoprotein made up of four identical subunits. Therefore, four biotin molecules are capable of binding to one avidin molecule, Adv. Prot. Chem. 29:85 (Green, N. M., 1975), thereby increasing the sensitivity of constructed probe systems, or allowing the crosslinking of 2 or more biotin-labeled materials.

The disassociation constant for the avidin-biotin complex is $10^{-15}$ at neutral pH, Biochem. J., 89:585 (Green, N. M., 1963). This interaction is one of the strongest non-covalent associations found in nature. Biotin is deeply bound in a groove in the avidin molecule with the carboxyl group about 9 angstroms below the protein surface, Biochem. J., 125:781 (Green, N. M., et al., 1971). The widespread use of biotin-avidin technology is based upon the fact that a biotin molecule is easily coupled via covalent linkage to a protein while maintaining substantially all the biological properties of the protein and also the binding capacity of biotin to avidin. However, steric hindrance can distort the biotin-labeled biomolecule when it is directly coupled to the biotin carboxyl group, causing decreased binding to avidin.

The introduction of an extended linking group can help eliminate steric impediments, Clin. Chem., 25: 1572 (Costello, S. M., et al., 1979), J. Immunol., 56:329 (Kentall, C., et al., 1983). Insertion of ε-aminocaproic acid (X-linker) as a spacer is one method of further separating the protein moiety of the biotinylated protein from the avidin molecule. One case where the insertion of an X-linker has been used is the study of biotinyl-insulin. Use of this X-linker between biotin analogs and insulin yielded complexes that were more stable than those lacking the spacer, Biochem. J., 21:978 (Hofmann, K., et al., 1982). Moreover, the use of an X-linker in biotinylated DNA probes enhanced the detectability of target DNA approximately fourfold. Proc. Natl. Acad. Sci., 80:4045 (Leary, J. J. 1983).

Biotin attached to a solid-support is described in Giese U.S. Pat. No. 4,282,287 with a continuation-in-part No. 4,478,914, (Giese) and a further continuation-in-part No. 4,656,252 (Giese). A precise layering technique wherein biotin is first attached to a solid-surface and the subsequent application of successive layers of avidin and extender, results in a controlled modification of surface characteristics.

European Patent No. 87,307,850.5 is directed toward a method for routine plant-virus diagnosis which includes biotin attached to a macro-molecule that is conjugated to a sample of probe DNA. The probe-containing-compound is applied to a solid-matrix which has a test sample of DNA derived from plant tissue immobilized thereon. The presence of the target sequence is determined by washing the matrix with enzyme-linked-avidin followed by assaying for enzyme activity associated with the matrix.

Galati et al. U.S. Pat. No. 4,467,031 described an enzyme-immunoassay which utilizes the biotin-avidin system as a convenient and stable linking group to connect a reporter enzyme to an antibody.

Hevey et al. U.S. Pat. No. 4,228,237 describes the use of the biotin-avidin system in a method for detection and determination of ligands. A surface having an antibody for the ligand of interest attached thereto is reacted with a sample of the ligand followed by a second-ligand-specific antibody that is conjugated with biotin. This coupling is then reacted with an avidin-conjugated-enzyme and results determined by measurement of enzyme activity.

Deutsch U.S. Pat. No. 4,656,025 describes a screening assay for tumor globulin. A tumor globulin-biotin conjugate on ELISA plates is reacted with avidin-conjugated-enzyme and quantification of the tumor globulin bound to the plate is determined by the application of the appropriate chromogenic substrate thereto.

Dressman et al. U.S. Pat. No. 4,535,057 describes an immunoassay having biotin conjugated to a solid support through an antibody-virus complex. This biotin-antibody virus complex is then reacted with avidin conjugated to a reporter group or a label and the presence of the label associated with the surface is indicative of the presence of virus in the sample.

Valkirs et al. U.S. Pat. No. 4,727,019, continuation-in-part of Valkirs et al. U.S. Pat. No. 4,632,901 describe an immunoassay wherein avidin is attached to a solid support and binds a ligand present in the sample to the support. U.S. Pat. No. 4,298,685 describes a diagnostic reagent that also involves avidin immobilized on a solid support. Rosentein U.S. Pat. No. 4,582,810 describes a detection system wherein a suspension of particles having avidin covalently bound thereto reacts with a biotin-antibody complex to form a still larger complex which results in a flocculent appearing solution.

Bacquet et al. U.S. Pat. No. 4,550,075 describes a method for ligand determination based on the biotin-avidin system without any solid support.

David et al. U.S. Pat. No. 4,486,530 describes an immunometric assay process that comprises a ternary complex of an antigenic substance and a first and second antibody bound to the antigen in which the complex is removed from solution by filtering through a membrane.

Clinical Chemistry 34, 8:1585 (Vilja et al. 1988) describes a monoclonal antibody based noncompetitive avidin-biotin assay for luteinizing hormone (LH) in urine.

Conventional methods for determining the incorporation of haptens into macromolecules involve assays such as the trinitrobenzene sulfonic acid (TNBS) assay (Snyder and Sobocinski, 1975, Analytical Biochemistry 64: 284–288) and assays based on ninhydrin (Samejima et al., 1971, Analytical Biochemistry 42: 237–247). The techniques involve the measurement of reactive groups present on the macromolecule of interest both before and after hapten or biotin derivatization. Incorporation of hapten or biotin is determined by difference. These conventional methods, however, are not very useful because they are destructive, inaccurate, and insensitive to the incorporation of small amounts of haptens, such as biotin, into large macromolecules.

Nucleic Acids Research 13: 745–761 (Forster et al., 1985) describes a photoactivatable biotin analogue, N-(4-azido-2-nitrophenyl)-N'-(N-d-biotinyl-3-aminopropyl)-N'-methyl-1,3-propanediamine (photobiotin). This compound may be used for the preparation of large amounts of stable, non-radioactive, biotin-labeled DNA and RNA hybridization probes. Upon irridation with visible light, photobiotin forms stable linkages with nucleic acids. Hybridization complexes produced from photobiotin and a nucleic acid are detected by avidin-alkaline phosphatase or other similar reagents.

Biotechnology 5: 269–272 (McInnes et al., 1987) presents hybridization analyses using photobiotin-labeled single- and double-stranded DNA probes which demonstrate that such probes possess the sensitivity required to replace radioactive probes in routine experiments and diagnostic assays.

SUMMARY OF THE INVENTION

Although methods exist for detecting specifically binding complexes in solution by the action of a diagnostic reagent, no method exists for accurately and non-destructively confirming whether the diagnostic reagent has been linked to protein or macromolecule.

Therefore, it is an object of the present invention to provide technology for accurately and non-destructively detecting the presence of a hapten linked to a molecule such as a protein or polynucleotide.

It is a further object of the present invention to provide technology for accurately and non-destructively determining the amount of hapten incorporated into molecules such as proteins or polynucleotides.

The present invention encompasses compounds comprising haptens such as biotin bound directly or indirectly to chromophoric group and a macromolecule-reactive group wherein the incorporation of the hapten in a protein or macromolecule can be confirmed directly by detecting the chromophoric group.

DETAILED DESCRIPTION OF THE INVENTION

Conventional methods for the determination of haptens incorporated into macromolecules such as proteins or polynucleotides are based on measuring primary amino groups on the macromolecule before and after reaction with a hapten. The difference in the amounts of primary amino groups represents the number of haptens incorporated into the macromolecule. However, these methods are inaccurate, destructive, and insensitive.

For example, assays based on trinitrobenzene-sulfonic acid (TNBS) destroy the biological properties of macromolecules. The present invention addresses this problem. It provides compounds and methods for incorporating a hapten into a macromolecule in a fashion that allows for direct determination of the amount of hapten incorporated while maintaining the biological properties of the macromolecule.

Thus, the present invention encompasses compounds comprising haptens bound directly or indirectly to chromophoric moieties, whereby the incorporation of the hapten into a protein or other macromolecule or fragments thereof can be confirmed by detecting the chromophoric moiety in a sensitive and non-destructive manner. More specifically, the compounds of the present invention, chromophoric hapten derivatives, comprise haptens bound by an extended linking group to a chromophoric group and a macromolecule-reactive group. The invention also encompasses methods for determining hapten amounts in macromolecules. An embodiment of the present invention may be viewed as follows:

where X is an extended linking group,
R is a chromophoric group, and
Y is a macromolecule-reactive group.

The macromolecule-reactive group may be an active ester and the hapten may be biotin as in the following:

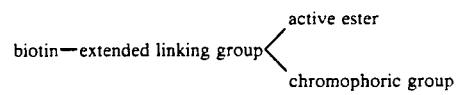

Macromolecules to be coupled to the chromophoric hapten derivatives may include proteins, (e.g., antibodies, lectins, DNA-binding proteins, etc.), RNA, DNA, polysaccharides (e.g., dextrans, agars etc.), or fragments of each.

Haptens (i.e., protein free substances which do not elicit antibody formation unless bound to a macromolecule carrier) which may be employed in the present invention are specific organic materials for which specific binding substances can be provided. A specific binding substance is any substance or group of substances having a specific binding affinity for the hapten to the exclusion of other substances. The employed hapten must be able to bind to a macromolecule or fragment thereof via an extender group. Examples of haptens which may be used according to the instant invention include steroids such as estrone, estradiol, testosterone, pregnanediol and progesterone; vitamins such as $B_{12}$, biotin and folic acid; triodothyronine, thyroxine, histamine, serotonine, digoxin, prostaglandins, adrenalin, noradrenalin, morphine, vegetable hormones' and antibiotics such as penicillin.

When the hapten is a substance having a naturally occurring receptor, the receptor can be utilized as the anti-hapten provided the receptor can be isolated in a form specific for the hapten. Illustrative haptens which have naturally occurring receptors include thyroxine, many steroids, polypeptides, such as insulin, angiotensin, avidin and many others. Receptors for this class of haptens are usually proteins or nucleic acids.

Extended linking groups are groups that will bind the hapten to the macromolecule or macromolecule fragment in such a way that the hapten is still able to undergo binding by an anti-hapten. Extended linking groups useful in the present invention include succinylated polylysine, dextran, polyethyleneglycol, and preferentially a polyamido ether extending group. These extended linking groups may be used separately or in combination to obtain extended linking groups of varying lengths and binding properties. Extended linking groups are preferred for use with serum samples and especially lipemic serum samples. Evidently, there are interfering substances in serum samples, the interference from which is overcome by the extended linking group. Where an extended linking group is not needed, a hapten such as biotin, without an extended binding group is bound to a functional group on a membrane or to a functional group on a protein which can be disbursed on the membrane.

The extended linking group must be able to also bind to the macromolecule or fragment. Preferentially the extended linking group having a hapten bound to one end will be bound to the protein or macromolecule with an amide bond; the amine of the amide bond arising from the protein and the carboxyl of the amide bond arising from the carboxy terminus of the extended linking group.

Various methods exist which may be employed to bind the extended linking group to a macromolecule or fragment. For example, to facilitate this binding the extended linking group may be attached to macromolecule-reactive groups such as active ester groups, amino groups, sulfhydryl groups, carbohydrate groups, azido groups or carboxy groups. A variety of methodologies exist for reacting macromolecule-reactive groups with macromolecules or macromolecule fragments. Examples of such methodologies are photo-crosslinking and glutaraldehyde crosslinking. Still other methods for effecting such coupling will occur to those skilled in the art. See, for examples of such methods, Ishikawa, J. Immunoassay, 4: 209–327 (1983) and Glazer et al., Labotatory Techniques in Biochemistry and Molecular Biology, North Holland Publishing, Amsterdam, 1975.

Active ester groups of the present invention should be selected such that they will not impair linkage of the extended linking group to a protein or macromolecule. Those skilled in the art will appreciate that active esters such as, for example, N-hydroxysuccinimide or N-hydroxysulfosuccinimide may be employed in the present invention. Alternatively, primary amino groups on the extended linking group may be coupled to primary amino groups on a protein by glutaraldehyde. Amino groups on proteins may be coupled to carboxy groups on the extended linking group. In addition, the extended linking group may be modified with a nitrophenyl azide such that coupling to a protein will occur when irradiated with visible light. Still other methods for effecting such coupling will occur to those skilled in the art.

The proteins and macromolecules of the present invention include, but are not limited to, bovine serum albumin (BSA), human chorionic gonadotropin (HCG), fibrinogen and immunoglobulin.

The anti-haptens of the present invention comprise the molecules described above that act as receptors to the above mentioned haptens.

Chromophoric groups suitable for use in the present invention may be selected from the group comprising various chromogenic substrates, dyes, dye intermediates, fluorescent or phosphorescent compounds. These chromophoric groups are molecules which absorb energy in the electromagnetic spectrum, usually in the ultraviolet and visible regions, and which may emit electromagnetic radiation at the same or a different wavelength.

Thus, chromophoric groups that may be employed in the present invention include derivatives of carboxytetramethyl-rhodamine, Texas Red, dinitrophenylaminohexanoic acid and other chromphores or fluorescent dyes. Other chromophoric moieties may be used in the present invention; however, these must be chosen such that the chromophoric group will not interfere with the binding of the hapten to the anti-hapten and will absorb energy at a different wavelength than the macromolecule to be labeled. Therefore, chromophoric groups that do not interfere in this interaction and that absorb at wavelengths greater than 300 nm are preferred for labeling proteins, polynucleotides, and fragments thereof. Determination of these chromophoric groups may be conveniently made by measuring chromophore absorbance, fluorescence, phosphorescence, or light scattering properties.

Accordingly, the present invention includes compounds of the formula:

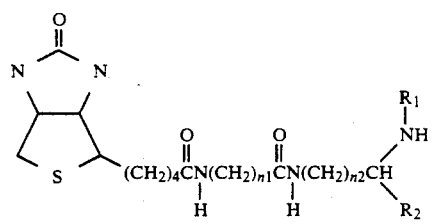

wherein
$n_1$ is 1, 2, 3, 4, 5, 6 or 7;
$n_2$ is 0, 1, 2, 3, 4, 5, 6 or 7;
$R_1$ is a carboxytetramethyl-rhodamyl, sulforhodamyl 101, or dinitrophenylaminohexanoyl group; and
$R_2$ is —$CO_2H$, —$NH_2$, —SH,

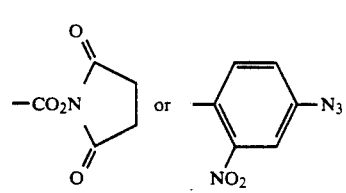

The invention is illustrated further by the following examples which are not to be construed as limiting the invention in scope or spirit to the specific procedures described in them.

EXAMPLE 1

A. Preparation of Lysyl-X-Biotin

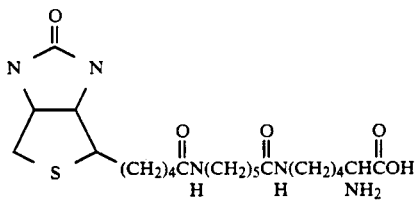

To a solution of 1.70 g (20.3 mmol) of sodium bicarbonate in 50 mL of water was added 5 g (20.3 mmol) of N-α-t-BOC-lysine. The pH was adjusted to 8 by the addition of sodium carbonate and a solution of 5.77 g (12.7 mmol) of succinimidyl-X-biotin (X-ε- aminocaproic acid) in 40 mL of dimethylformamide was added. The reaction was stirred at room temperature for 16 hours and the solvent was removed under reduced pressure. The residue was triturated with 150 mL of a 10% citric acid solution and the resulting suspension was cooled overnight at 4° C. The colorless solid was collected and washed with water. Deprotection of this material was effected by stirring in a solution of 50 mL of concentrated hydrochloric acid in 200 mL of dioxane for 20 minutes at room temperature. The addition of 800 mL diethyl ether gave a solid which was collected and washed with diethyl ether. The crude product was dissolved in 70 mL of hot water at a pH of 2 and any color was removed with activated charcoal. Adjusting the pH to 4.5 and cooling yielded 2.2 g of a colorless solid. A second crop of 0.7 g was also obtained. The purity of these materials was determined by TLC on silica gel: $R_f=0.64$ (chloroform: methanol: water; 2:3:1). $^1$H NMR (D$_2$O); δ1.2-1.8(m, 18H), 2.22(m, 4H), 2.63(dd,1H), 2.86(dd,1H), 3.16(m, 4H), 3.32(m,1H), 3.51(m,1H,C$_{25}$), 4.4(m,1H), 4.6(m,1H).

B. Preparation of Dinitrophenyl Aminohexanoyl (DNP)-Lysyl-X-Biotin

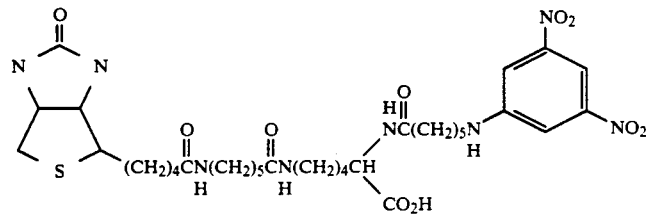

To a suspension of 2.00 g (4.12 mmol) of lysyl-X-biotin in 240 mL of water, was added 1 mL of ethyl-diisopropyl amine. The mixture was stirred for 10 minutes at room temperature to yield a homogeneous solution. After this solution was diluted with 450 mL of dimethylformamide, cooled to room temperature in an ice bath, a solution of 1.80 g (4.56 mmol) of succinimidyl-6-(N-(2,4-dinitrophenyl)amino)hexanoate in 160 mL of dimethylformamide was added. The reaction mixture was stirred at room temperature for 3 hours and the solvent was removed under reduced pressure. The residue was dissolved in 600 mL of 10 mM ammonium hydroxide and the resulting solution was washed five times with 100 mL portions of chloroform. The pH of the aqueous solution was adjusted to 2 with a 10% hydrochloric acid solution, which precipitated a yellow oil. The water portion was decanted and was extracted four times with a 25% methanol in chloroform solution. The extract was combined with a methanol solution of the above oil. The resulting cloudy solution was filtered through cotton and the solvent was removed under reduced pressure to yield a yellow gum. Trituration with diethyl ether yielded a solid. This was collected, washed with diethyl ether and dried under pressure to yield 3.00 g of a yellow powder. The purity of this material was determined by TLC on silica gel. (chloroform: methanol: acetic acid, 90:30:6).

C. Preparation of Succinimidyl-(DNP)-Lysyl-X-Biotin

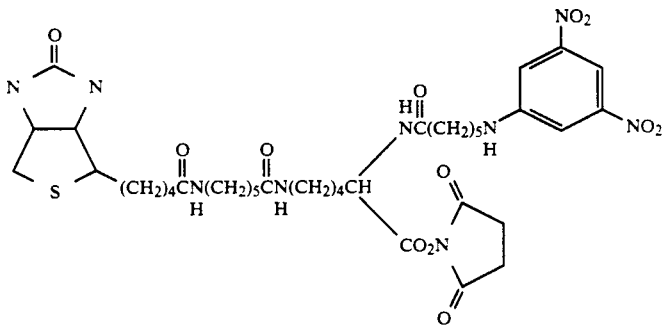

To a solution of 1.50 g (1.96 mmol) of DNP-lysyl-X-biotin in 40 mL of dry dimethylformamide was added 24 mg (0.19 mmol) of 4-dimethylaminopyridine and 550 mg (2.15 mmol) of disuccinimidyl carbonate. The resulting solution was allowed to stir at room temperature. Three additional portions of disuccinimidyl carbonate (50 mg) were made at one hour intervals. One hour after the final addition, the reaction mixture was added to 400 mL of vigorously stirred diethyl ether. The product deposited onto the sides of the vessel over time and the diethyl ether was decanted. Trituration of the resulting gum with ether gave a solid. The solid was collected, washed with ether and dried under reduced pressure to yield 1.50 g of the desired product as a yellow powder. The purity of this material was determined by TLC on silica gel. (chloroform: methanol: acetic acid; 80:18:4).

EXAMPLE 2

Biotinylation of BSA with Succinimidyl-Rhodamyl-Lysyl-X-Biotin

NHS (Rhodamyl)LX-Biotin

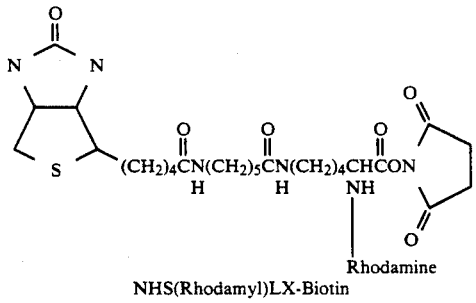

NHS(Rhodamyl)LX-Biotin

NHS(Rhodamyl)LX-Biotin was prepared in a fashion similar to that used for the preparation of succinimidyl-(DNP)-lysyl-X-biotin. Bovine serum albumin (BSA) (500 uL of 1 mg/ml BSA in PBS) was added to 20 μl of a NHS(Rhodamyl)LX-Biotin/dimethylformamide (DMF) solution. The NHS(Rhodamyl)LX-Biotin/DMF solutions were prepared to yield final molar ratios of NHS(Rhodamyl)LX-Biotin to BSA of 5, 10, 20 and 80 to 1. After reaction at room temperature for 80 minutes, the mixtures were chromatogaphed on a PD-10 disposable Sephadex G-25 column (Pharmacia, Piscataway, N.J.). The colored material eluting in each void volume contained derivatized BSA. Free rhodamyl-lysyl-X-biotin was retained on the column and collected in later fractions. The biotinylated-BSA fractions were pooled and the spectrum of the combined fractions measured to calculate the number of biotin molecules per BSA molecule. A control experiment was performed using hydrolyzed rhodamyl-lysyl-X-biotin (hydrolyzed to remove the succinimide moiety at 0.6 mg/ml in PBS, 37°, 4.5 hour) and reacted with BSA at 20 to 1 ratio of rhodamyl-lysyl-X-biotin to BSA. The results are summarized in Table I.

TABLE I

| Molar Ratio of NHS(Rhodamyl)LX-Biotin to BSA in reaction Mixture | Resulting Molar Ratio of Biotin to BSA in Derivative |
|---|---|
| 5:1 | 1 |
| 10:1 | 1 |
| 20:1 | 2 |
| 80:1 | 4 |
| Control 20:1 | <0.2 |

EXAMPLE 3

Biotinylation of IgG

An affinity purified, IgG fraction of goat anti-α-hCG (human chorionic gonadotropin) was obtained from BiosPacific (Emeryville, Calif.) Anti-hCG IgG (500 μl of 0.5 mg/ml in PBS) was added to 20 μl of a of NHS(Rhyodamyl)LX-Biotin/dimethylformamide solution and incubated at 37° for 1 hour. This procedure was performed using NHS(Rhodamyl)LX-Biotin/DMF solutions prepared to yield final molar ratios of NHS(Rhodamyl)LX-Biotin to IgG of 10 and 20 to 1. After column chromatography to remove the free rhodamyl-lysyl-X-biotin, the biotinylation ratio was calculated and summarized in Table II:

TABLE II

| Molar Ratio of NHS(Rhodamyl)LX-Biotin To IgG in Reaction Mixture | Resulting Molar Ratio of Biotin to IgG in Derivative |
|---|---|
| 10:1 | 2 |
| 20:1 | 3 |

EXAMPLE 4

Detection of HCG with Rhodamyl-Lysyl-X-Biotin Derivatized Anti-hCG

50 μl of PBS diluent (0.1% BSA, 0.25% Triton X-100 in PBS) prepared to contain 0 or 1 ng of hCG was added to 100 μl of a solution containing 250 ng rhodamyl-lysyl-X-biotin derivatized anti-α-hCG IgG (prepared as in Example 3) and 5 ng fluorescein derivatized-anti-β-hCG and mixed with 100 μl of a PBS solution containing 0.5 μg streptavidin and 0.5 μg of urease-conjugated-anti-fluorescein IgG. This mixture was incubated at 37° for 1 hour. After incubation, 1 ml of PBS diluent was added and the entire mixture was filtered through a biotin-derivatized membrane (Molecular Devices Corp., Menlo Park, Calif.). The immune complex was captured on the membrane and the unbound material removed by washing with 2 ml of wash solution prepared to contain 10 mM sodium phosphate, 0.1M NaCl, 0.05% surfactant such as polyethylene oxide sorbitan mono-oleate (pH 6.5). The amount of urease bound to the membrane was quantitated with a Threshold TM system of the type described in U.S. Pat. No. 4,591,550. The electronic signal (μv/sec) was proportional to the sample hCG content and the results are shown in Table III.

TABLE III

| Sample HCG (ng) | Signal (μv/sec) |
|---|---|
| 0 | 54 |
| 1 | 713 |

EXAMPLE 5

Biotinylation of Protein with Succinimidyl-(Texas Red) Lysyl-X-Biotin [NHS(TR)LX-Biotin]

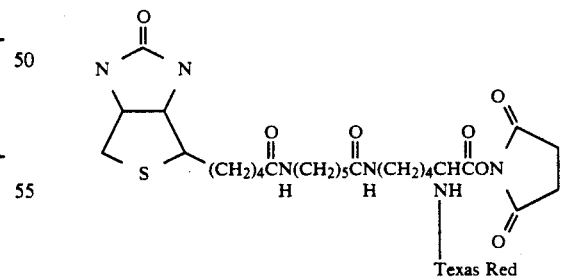

NHS(TR)LX-Biotin, prepared by a method similar to that for succinimidyl-(DNP)-lysyl-X-biotin, was dissolved in DMF and added to appropriate amounts of a 1 mg/ml protein solution. The final DMF concentration in each mixture was adjusted to 4%.

The mixture was then incubated at room temperature for 2 hours and run through a PD-10 column (Pharmacia) to separate the derivatized protein from free Texas Red-lysyl-X-biotin.

The optical densities were measured at 280 and 592 nm to determine the coupling ratio of biotin molecules per protein. The results are displayed in Table IV.

TABLE IV

| Molar Ratio of NHS(TR)LX-Biotin Reaction Mixture | Resulting Molar Ratio of Biotin Molecules To Protein In Derivative |
|---|---|
| BSA 5:1 | 1 |
| BSA 10:1 | 2 |
| Mouse IgG, 10:1 | 2 |
| Mouse IgG, 20:1 | 2 |
| Goat Anti-mouse IgG (Fc specific), 10:1 | 3 |
| Goat anti-mouse IgG (Fc specific), 20:1 | 4 |

EXAMPLE 6

Use of NHS(TR)LX-Biotin for Assay of Mouse IgG

Goat anti-mouse IgG, (Fab')2 specific, was labeled with fluorescein-X-NHS to 3 fluorescein per antibody. Goat anti-mouse IgG, Fc specific, was labeled with NHS(TR)LX-Biotin to 3 biotins per IgG. For comparison purposes, the same IgG was labeled with NHS-X-biotin to 3 biotins per IgG.

100 μl of sample (0 or 500 pg mouse IgG) was then incubated with 100 μl of labeled antibodies (20 ng of fluoresceinated antibody and a varying amount of biotinylated antibody), and 100 μl enzyme reagent (containing 1 μg streptavidin and 2 μg urease-anti-fluorescein) at room temperature for 1 hour. This mixture was filtered through a biotin-derivatized membrane which was washed with 2 mL of wash solution (as in Example 4). The membrane was inserted into a Threshold TM system and the signal read as described in Example 4. The results are shown below in Table V.

TABLE V

| Derivatized Anti-(mouse IgG) per Assay | Signal (μv/sec) | |
|---|---|---|
| | 0 pg | 500 pg |
| IgG-(Texas Red) Lysyl-X-Biotin, 50 ng | 66 | 223 |
| IgG-(Texas Red) Lysyl-X-Biotin, 100 ng | 60 | 263 |
| IgG-(Texas Red) Lysyl-X-Biotin, 200 ng | 80 | 351 |
| IgG-X-Biotin, 100 ng | 90 | 653 |

EXAMPLE 7

Biotinylation of Anti-MuIgG with Succinimidyl-(DNP)-Lysyl-X-Biotin NHS(DNP)LX-Biotin Anti-mouse IgG (anti-MuIgG) was added to a NHS(DNP)LX-Biotin/DMF solution and incubated at room temperature for 2 hours. This procedure was performed with DMF solutions prepared to yield biotinylated anti-MuIgG having biotin:protein ratios of 5:1 and 2:1 respectively. The resulting reaction mixtures were column chromatogaphed to remove any remaining or hydrolysed NHS(DNP)LX-Biotin. The labeled IgG was then used in Example 8.

EXAMPLE 8

Use of NHS(DNP)LX-Biotin for Assay of Mouse IgG

A 100 μl sample of mouse IgG was combined with NHS(DNP)LX-biotin labeled anti-mouse IgG, fluorescein-labeled anti-mouse IgG, and 100 μl of reagent containing 1 μg streptavidin and 2 μg urease-anti-fluorescein. The resulting mixture was incubated at room temperature for 1 hour.

The incubated mixture was filtered through a biotin containing membrane. The membrane was subsequently washed with 2 mL of wash solution (as in Example 4) and inserted into a Threshold TM sensor as described in Example 4. The signal was then read generating the results in Table VI.

TABLE VI

| IgG Label Used | Biotin to IgG Molar Ratio | Labeled IgG (ng) used in assay | Measured signal (μv/sec) | |
|---|---|---|---|---|
| | | | −MuIgG (0 pg) | +MuIgG (1000 pg) |
| NHS-X-Biotin (control) | 2 | 100 | 178 ± 7 | 1013 ± 32 |
| NHS(DNP)LX-Biotin | 2 | 50 | 160 ± 4 | 587 ± 13 |
| | | 100 | 186 ± 2 | 770 ± 46 |
| | | 200 | 197 ± 3 | 938 ± 13 |
| NHS(DNP)LX-Biotin | 5 | 50 | 161 ± 3 | 491 ± 25 |
| | | 100 | 182 ± 3 | 729 ± 1 |
| | | 200 | 182 ± 4 | 989 ± 10 |

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound of the formula:

$$\text{structure with } (CH_2)_4CN(CH_2)_{n_1}CN(CH_2)_{n_2}CH$$

wherein
$n_1$ is 1, 2, 3, 4, 5, 6 or 7;
$n_2$ is 0, 1, 2, 3, 4, 5, 6 or 7;
$R_1$ is either a carboxytetramethyl-rhodamyl, sulforhodamyl 101, or dinitrophenylaminohexanoyl group; and
$R_2$ is —CO$_2$H, —NH$_2$, —SH, —CO$_2$N(succinimidyl) or dinitrophenyl-azide group.

* * * * *